US011173260B2

(12) United States Patent
Golovanova et al.

(10) Patent No.: US 11,173,260 B2
(45) Date of Patent: Nov. 16, 2021

(54) AEROSOL GENERATING DEVICE HAVING VAPOUR-COOLING PASSAGEWAY

(71) Applicant: JT International S.A., Geneva (CH)

(72) Inventors: Tatiana Golovanova, Genthod (CH); Christopher Rory Parsons, Belfast (IE); Michael Orth, Trier (DE); Takashi Hasegawa, Geneva (CH); Michael Plattner, Trier (DE); Thomas Johaentges, Schweich (DE)

(73) Assignee: JT International S.A.

( * ) Notice: Subject to any disclaimer, the term of this patent is extended or adjusted under 35 U.S.C. 154(b) by 590 days.

(21) Appl. No.: 16/063,492

(22) PCT Filed: Dec. 12, 2016

(86) PCT No.: PCT/EP2016/080604
§ 371 (c)(1),
(2) Date: Jun. 18, 2018

(87) PCT Pub. No.: WO2017/102633
PCT Pub. Date: Jun. 22, 2017

(65) Prior Publication Data
US 2018/0368478 A1 Dec. 27, 2018

(30) Foreign Application Priority Data

Dec. 18, 2015 (GB) ..................... 1522368

(51) Int. Cl.
*A24F 13/00* (2006.01)
*A24F 17/00* (2006.01)
(Continued)

(52) U.S. Cl.
CPC ............... *A61M 15/06* (2013.01); *A24F 7/02* (2013.01); *A24F 40/485* (2020.01);
(Continued)

(58) Field of Classification Search
CPC ......... A24F 47/00; A61M 11/04; A61M 15/06
(Continued)

(56) References Cited

U.S. PATENT DOCUMENTS 8,851,083 B2* 10/2014 Oglesby ............... A61M 11/042
　　　　　　　　　　　　　　　　　　　　131/271
8,869,792 B1 10/2014 Lee
(Continued)

FOREIGN PATENT DOCUMENTS

| EP | 2719415 A1 | 4/2014 |
| WO | 2007012007 A2 | 1/2007 |
| WO | 2015101479 A1 | 7/2015 |

OTHER PUBLICATIONS

International Search Report including Written Opinion for PCT/EP2016/080604 dated May 4, 2017.

*Primary Examiner* — Abdullah A Riyami
*Assistant Examiner* — Thang H Nguyen (57) ABSTRACT

An aerosol generating device, includes an inhalation outlet; a chamber for holding a material, the material capable of generating a vapour when heated; a heater for heating material held in the chamber; an air inlet connected by an air inlet passage to the chamber; a vapour-cooling module providing a fluidic connection between the chamber and inhalation outlet, the module configured to cool a vapour passing there through. Suction at the inhalation outlet causes air to enter the chamber via the air inlet, thereby transporting vapour generated in the chamber through the module to the inhalation outlet, such that the temperature of the vapour exiting the device through the inhalation outlet is substantially lower than the temperature of the vapour generated in the chamber. The device thereby provides a means whereby a vapour generated in the chamber is substantially cooled during transport from the chamber through the mouthpiece to the user.

25 Claims, 6 Drawing Sheets

(51) Int. Cl.
   *A24F 25/00*      (2006.01)
   *A61M 15/06*      (2006.01)
   *A61M 11/04*      (2006.01)
   *A61M 15/00*      (2006.01)
   *A24F 40/485*     (2020.01)
   *A24F 7/02*       (2006.01)
   *A24F 40/20*      (2020.01)

(52) U.S. Cl.
   CPC ...... *A61M 11/042* (2014.02); *A61M 15/0021* (2014.02); *A61M 15/0036* (2014.02); *A61M 15/0086* (2013.01); *A24F 40/20* (2020.01); *A61M 2205/123* (2013.01); *A61M 2205/3606* (2013.01); *A61M 2205/3653* (2013.01); *A61M 2205/8206* (2013.01); *A61M 2206/12* (2013.01)

(58) Field of Classification Search
   USPC .......................................................... 131/329
   See application file for complete search history.

(56) References Cited

U.S. PATENT DOCUMENTS

| | | | |
|---|---|---|---|
| 10,206,430 B2* | 2/2019 | Mironov | A61M 11/08 |
| 2015/0020822 A1* | 1/2015 | Janardhan | A61M 15/06 |
| | | | 131/328 |
| 2016/0073694 A1* | 3/2016 | Liu | A24F 40/485 |
| | | | 131/329 |
| 2016/0120221 A1* | 5/2016 | Mironov | A24F 40/465 |
| | | | 392/395 |
| 2017/0027233 A1* | 2/2017 | Mironov | A24F 40/465 |
| 2017/0079110 A1* | 3/2017 | Plattner | A61M 11/042 |
| 2017/0079330 A1* | 3/2017 | Mironov | A24F 40/90 |

\* cited by examiner

AEROSOL GENERATING DEVICE HAVING VAPOUR-COOLING PASSAGEWAY

The present invention relates to an aerosol generating device for heating a material to release an inhalable vapour.

Aerosol generating devices such as electronic cigarettes which generate a vapour from a liquid are relatively well known and are becoming increasingly popular. Another type of aerosol generating device uses controlled-temperature heating whereby a smokable material, such as tobacco, is heated sufficiently to release a vapour but without increasing the heating temperature to a level at which the material burns. Such devices therefore have the advantage of generating an inhalable vapour without requiring burning of the material.

Prior art devices generally comprise a controlled-temperature heating chamber connected to a mouthpiece via an inhalation channel, wherein the heating chamber is configured to accept a replaceable cartridge of smokable material. A user places a cartridge of material into the chamber and inhales at the mouthpiece whilst activating the heater to draw a vapour, generated in the chamber, through the mouthpiece for inhalation. There are however several ongoing problems with such conventional devices.

One issue associated with such devices is that the generated vapour exits the device at an elevated temperature meaning inhalation of the vapour can be sub-optimal. Although some prior art devices provide an air inlet, through which ambient air may mix with and thereby cool the generated vapour, such a configuration means the generated vapour is heavily diluted which may not be satisfactory to the user. Furthermore the cooling effects of introducing ambient air into the chamber may not be sufficient to cool the vapour to an optimal temperature for inhalation.

One difficulty associated with cooling the generated vapour is that this is liable to produce condensation within the internal passageways of the device. If the condensation is left within the device, after continued use this may result in the increased degradation of the internal components of the device or have a detrimental effect on flavour or hygiene.

There accordingly exists a need for a heating without burning aerosol generation device, in which the generated vapour characteristics are significantly improved. In particular there exists a need to provide such a device in which the generated vapour is significantly cooled after generation before it is inhaled. There further exists a related need to avoid the detrimental effects of condensation produced within the device.

The present invention seeks to provide a controlled temperature aerosol generating device configured to heat without burning a material which may provide a cool vapour to a user whilst minimising the effects of condensation, overcoming the problems of the prior art.

According to the present invention there is provided an aerosol generating device, comprising an inhalation outlet; a chamber for holding a material, the material capable of generating a vapour when heated; a heater for heating material held in the chamber; an air inlet connected by an air inlet passage to the chamber; a vapour-cooling module providing a fluidic connection between the chamber and inhalation outlet, the module configured to cool a vapour passing there through; wherein, in use, suction at the inhalation outlet causes air to enter the chamber via the air inlet, thereby transporting the vapour generated in the chamber through the vapour-cooling module to the inhalation outlet, such that the temperature of the vapour exiting the device through the inhalation outlet is substantially lower than the temperature of the vapour generated in the chamber.

With the aerosol generating device according to the present invention it is possible to provide a means whereby a vapour generated in the chamber is substantially cooled during transport from the chamber through the mouthpiece to the user. Since this mechanism does not rely on the addition of ambient air via air inlets to cool the vapour, the temperature of the vapour may be reduced independently of the concentration of the vapour, unlike prior art devices. Examples of the invention further provide a modular vapour cooling component which may enhance collection of condensation droplets within the device and which may be cleaned or replaced in a straightforward manner, allowing the detrimental effects of condensation to be reduced.

One example of the present invention will now be described with reference to the accompanying drawings, in which.

Figure 1A:
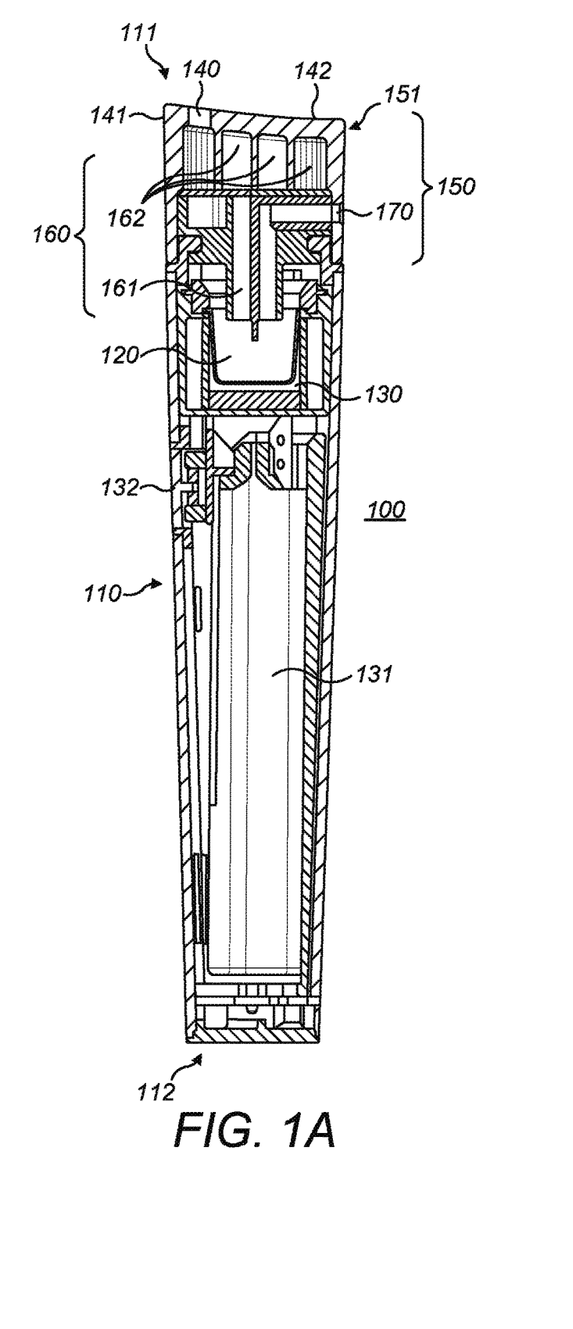
FIGS. 1A and 1B show a cross section of an aerosol generating device according to the present invention.
Figure 1B:
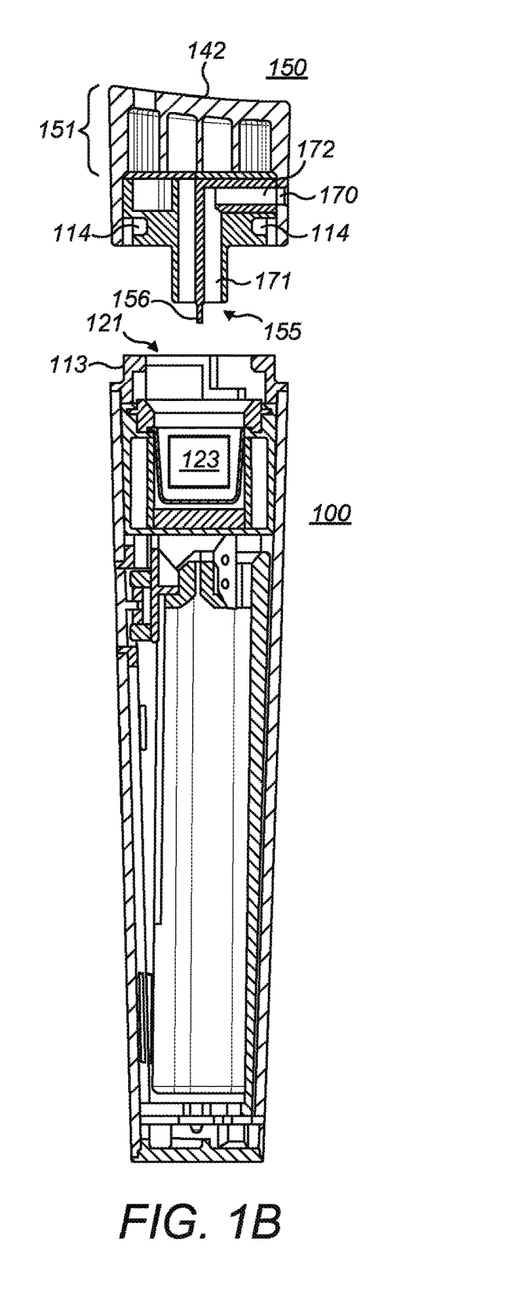

Referring to FIG. 1, an example of an aerosol generating device 100 according to the present invention comprises an elongate body 110 having a first 111 and second 112 end. The aerosol generating device 100 further comprises a chamber 120 and a heater 130 configured to heat a material held in the chamber 120. The heater 130 is preferably configured to heat the material in the chamber to a temperature sufficient to release vapour but is restricted from exceeding a temperature at which the material burns. An inhalation outlet 140 is positioned near the first end 111 of the device 100 and a vapour-cooling module 150 is positioned between the chamber 120 and inhalation outlet 140. A vapour-cooling passageway 160 runs through the vapour cooling module 150 providing a fluidic connection between the chamber 120 and inhalation outlet 140.

In the exemplary device of FIG. 1, the cooling function of the vapour-cooling module 150 is provided by utilising a vapour-cooling passageway 160 of sufficient length such that a vapour is significantly cooled during passage of the vapour through the vapour cooling passageway 160, as will be discussed in more detail below. In this example, the extended vapour cooling passageway 160 has two portions, the first portion 161 extending in a direction along the elongate axis of the device between the chamber and end portion 151 of the vapour cooling module 150. The second portion 162 of the vapour cooling passageway is coiled in a planar section 151 of the vapour cooling module, in a plane substantially normal to the elongate axis of the device. As will be discussed in detail, this arrangement has the advantage of allowing for a substantially longer vapour cooling passageway 160 without significantly extending the required length of the device 100.

FIG. 1 further shows an air inlet 170, in this example positioned on the vapour cooling module 150, connected to the chamber 120 via an air inlet passage having two portions: a first portion 171 extending substantially parallel to the first portion 161 of the vapour cooling passageway 160 into the chamber 120 and a second portion 172 extending substantially perpendicular to the first portion 161 of the vapour cooling passageway 160 in connection with the air inlet 170.

The heater 130 of this example is formed of heating plates substantially surrounding the chamber on all sides other than the side interfacing with the vapour cooling passageway 160 of the vapour cooling module 150. This arrangement allows for heating over a large proportion of the surface area of the chamber 120, facilitating a uniform constant heating and thus aiding in maintaining the controlled temperature in the chamber 120 necessary to heat the material contained therein to a specific temperature without burning the material. Alternatively the chamber may be formed by a conductive shell which is heated to provide the required uniform heating. The heater of this example is an electric heater powered by a battery 131 disposed in the lower portion of the device towards the second end 112. The heater 130 may be actuated by a user implemented heating button 132, as shown in FIG. 1, or by other trigger means, such as a flow sensor actuated by a user inhaling at the inhalation outlet 140.

As illustrated in FIG. 1, the vapour cooling module 150 may be positioned at a first, proximal end 111 of the device 100, with the inhalation outlet 140 provided on a top, end surface 142 of the module 150. In such an arrangement, the vapour cooling module 150 itself may act as a mouthpiece, without requiring an additional mouthpiece unit configured to interface with the module 150, upon which the user may draw to inhale the vapour. However in other examples a mouthpiece unit may connect to the top side 111 of the vapour cooling module 150 to provide this function. In the case of the vapour cooling module 150 itself providing the mouthpiece, an edge of the end surface 142 may curve up into an outward protrusion 141 upon which the inhalation outlet 141 is placed, so as to achieve a more ergonomic shape to allow a user to form a tighter seal with their lips around the device and facilitate inhalation of the vapour.

Shown in the exemplary device of FIG. 1B, the vapour cooling module 150 may form a detachable portion of the device body 110. This arrangement allows for the vapour cooling module to be removed in order to expose an opening 121 to the chamber 120. In this way a user may fill, replace or replenish the material held within the chamber 120. The refill may be in the form of a cartridge 123 as schematically illustrated in FIG. 1B. A protrusion 155 extends from the vapour cooling module such that bringing the module into contact with the opening to the chamber causes the protrusion to extend into the chamber 120. As clearly illustrated in FIG. 1B, both the first portion 161 of the vapour cooling passageway 160 and the first portion 171 of the aft inlet passage are provided within the protrusion 155, thereby enabling the passage of ambient air into the chamber and generated vapour out of the chamber.

The protrusion 155 of the vapour cooling module 150 also serves a secondary purpose. It is known in the prior art to facilitate replacement of the smokable material in the chamber 120 by utilising a cartridge containing the material. Such a cartridge may have an outer wrapping surrounding a compressed block of smokable material such as tobacco. A cartridge may therefore firstly be placed into the chamber 120 with the vapour cooling module 150 removed, after which the module 150 is reconnected to the device 100. The action of bringing the module 150 into connection with the exposed opening 121 in body 110 of the device would then bring the protrusion into contact with the cartridge, piercing the wrapping of the cartridge and forming the ambient air passageway into the cartridge and the vapour cooling passageway out of the cartridge into the vapour cooling module.

Figure 2A:
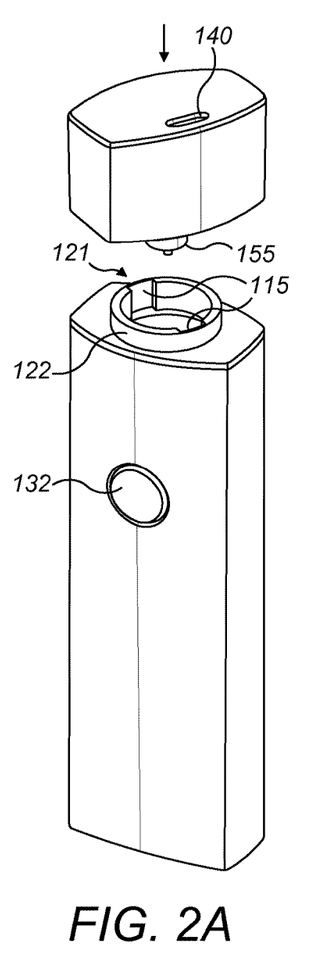
FIG. 2 shows a connection means of a vapour cooling module and an aerosol generating device according to the present invention.
Figure 2B:
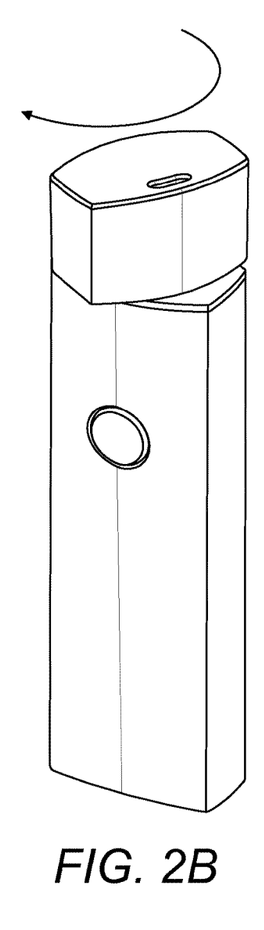
Figure 2C:
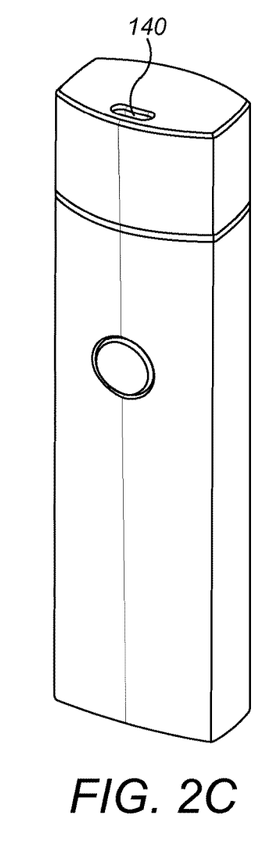

The releasable attachment may be provided by a "twist and lock" mechanism, as illustrated by FIG. 2. It may further be provided by magnets as will be discussed in relation to FIG. 6. The mechanism is provided by axially aligned recesses 115 in a collar portion 122 around the opening 121 to the chamber 120. These recesses 115 may be matched to the cross sectional shape of the protrusion 155 thus only allowing the protrusion 155 to enter the chamber opening 121 in a certain rotational orientation about the elongate axis of the device. Once the vapour cooling module has been brought onto the body of the device in the correct rotational orientation, the module may be rotated (illustrated in FIG. 2B) bringing internal protrusions 113 in the body of device into contact with corresponding interlocking recesses 114 internal to the module, thereby locking the module into place in a position in which it is aligned with the body of the device, as shown in FIG. 2C.

Figure 3:
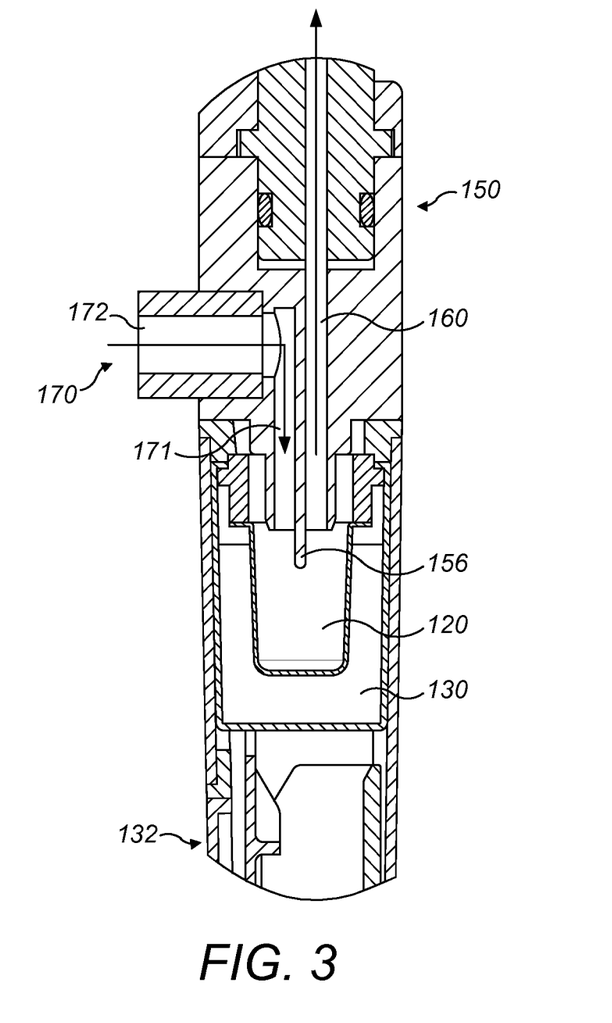
FIG. 3 shows the air and vapour flow through an aerosol generating device according to the present invention.

The flow of air and vapour during operation of an aerosol generating device 100 according to the present invention is illustrated in FIG. 3. When the heater 130 is actuated the temperature of the heating plates rises to a temperature sufficient to heat the material within the chamber 120 to a level whereby it releases vapour without burning. Upon inhalation at the air inhalation outlet, ambient air enters through the air inlet 170 and passes along the second portion 172 of the air inlet passageway laterally into the device. The ambient air then passes along the first portion 171 of the air inlet passage which carries the ambient air along the elongate axis of the device, through the protrusion 155 directly into the chamber 120. Aligning the chamber-interfacing portion of the air inlet passage in this way ensures the ambient air penetrates deeper into the chamber 120, enhancing extraction of the vapour. The ambient air mixes with the vapour generated from the material in the chamber 120 and this mixture travels out of the chamber 120 along the vapour cooling passageway 160 for inhalation through the inhalation outlet 140. The aerosol (also referred to as a vapour) exiting the device is therefore a combination of the vapour generated in heating of the material mixed with ambient air introduced through the air inlet 170.

The extraction of vapour may be improved further by providing an extended divider 156 between the first portion 171 of air inlet passage and vapour cooling passageway 160 which extends beyond the openings to the passageways, deeper into the chamber 120. Using this arrangement the ambient air from the air inlet passageway must travel deeper into the chamber before exiting through the vapour cooling passageway 160.

The vapour cooling passageway 160 must be of sufficient length such that the temperature of the relatively hot vapour generated in the chamber may be reduced during passage along the vapour cooling passageway to an optimal level for inhalation at the outlet. The precise length necessary to achieve this will depend on a number of factors such as the materials used to construct the components, the diameter of the vapour cooling passageway, the heating temperature and size of the air inlet 170. However the length required may be determined in a straightforward manner by routine experiment for any specific values of these factors. For a vapour cooling passageway diameter of around 4.5 mm and a heating temperature appropriate to release vapour from tobacco without burning, a vapour cooling passageway length of 90 mm or greater was required to sufficiently cool the vapour to an optimal temperature. The characteristics of the inhaled vapour are improved if the vapour cooling passageway between the chamber and inhalation outlet is substantially longer than the air inlet passageway.

As will be discussed, the vapour cooling passageway 150 may take one of a number of configurations as long as they are appropriate to provide the essential function of cooling the generated vapour. As indicated in FIG. 3, the vapour cooling passageway 160 may simply extend linearly along the elongate axis of the device between the chamber 120 and inhalation outlet 140. However since this may extend the length of the device beyond dimensions acceptable to a user, there are a number of other configurations which may more efficiently utilise the space within the module to provide an extended vapour cooling passageway which is constrained to more acceptable dimensions.

Figure 4A:
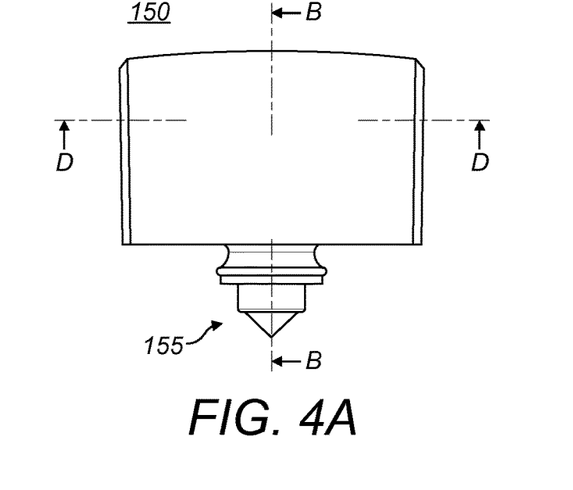
FIG. 4A shows a side view of a vapour cooling module according to the present invention.

As discussed with reference to FIG. 1, one possible vapour cooling module 150 arrangement configuration utilises a coiled vapour cooling passageway to maximise the length of passageway within a substantially planar section of the module. Such a coiled passageway arrangement is illustrated in FIG. 4. FIG. 4A shows an external side view of an exemplary vapour cooling module with a plan and side section indicated, the corresponding views of which are shown in FIGS. 4B and 4C respectively.

Figure 4B:
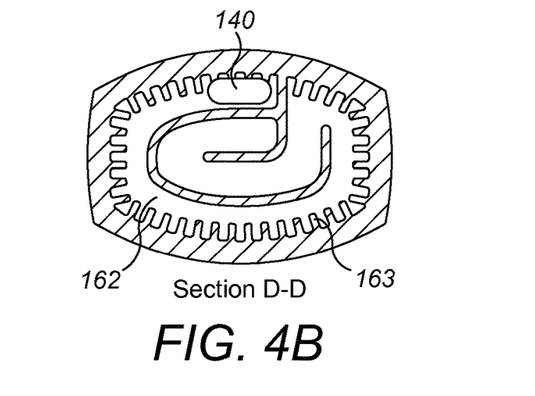
FIG. 4B shows a cross section of a vapour cooling module according to the present invention.
Figure 4C:
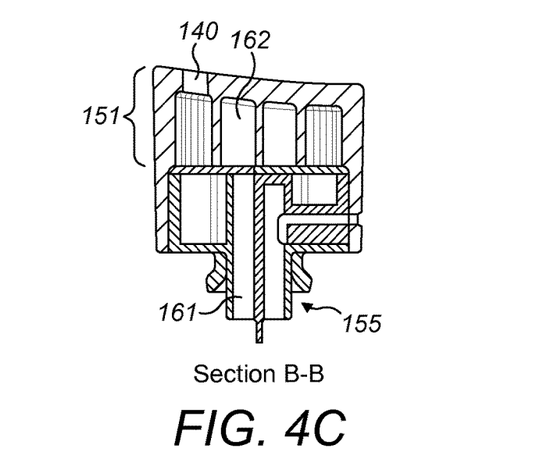
FIG. 4C shows an end section of a vapour cooling module according to the present invention.

The plan section through the top portion 151 of the vapour cooling module, shown in FIG. 4B, clearly illustrates the coiled arrangement of the vapour cooling passageway 160. In this arrangement, the second portion 162 of the vapour cooling passageway 160 is coiled around itself with the coiled path lying in a plane perpendicular to the elongate axis of the device, confined to a top planar section 151 of the module. This arrangement clearly makes most efficient use of the space available, filling the cross-sectional area of top section to maximise the length of the vapour cooling passageway 160 whilst minimizing the required extension in length of the module itself. FIG. 4C shows how aft enters the coiled section of the second portion 162 through an initial straight first portion 161 which runs through the protrusion 155 of the module. This first portion 161 is in fluidic connection with the second portion 162 in the centre of the module. The second portion 162 then coils around itself, the coiled path confined to the plane of the top portion 151 of the module before reaching the inhalation outlet 140 at a radial extremity of the module 150.

The curved path of the second portion 162 provided within a planar section 151 of the vapour cooling module 150 has further advantages beyond that of making the most efficient use of space such that the overall length of device may be minimised, as described above. This top planar section 151 may form a removable component which can be replaced or cleaned. This is particularly important to prevent the build-up of condensation which may have a detrimental effect on device performance and vapour flavour, as discussed below. In contrast to examples in which curved path portion extends over the length of the module, by providing a section, preferably a top section, of the vapour cooling module in which the curved passageway is positioned, cleaning may be carried out in a much more straightforward manner. It further means that if this portion needs to be replaced after a certain amount of use, this may be achieved whilst retaining several components of the vapour cooling module which may be more robust to degradation and have a longer lifetime.

The exact arrangement of the second portion 162 of the vapour cooling passageway 160 may take a number of different configurations. In the example of FIGS. 1, 2 and 4 in which the cross sectional shape of the module is a rounded rectangle, the increased aspect ratio means that the space is more effectively filled by the path first coiling anticlockwise before turning back on itself and following a curved clockwise path to reach the inhalation outlet 140. However in other examples, for example in a device with a circular cross section or with an aspect ratio closer to 1, it may be more effective for the coiled section of the passageway to follow a spiral shape, winding around the centre point in a gradually widening curve about the centre point before meeting the inhalation outlet 140.

As illustrated in FIG. 4B, the internal surfaces of the vapour cooling passageway may be ridged with a periodic array of projections 163. Such variations of the cross sectional area of the vapour cooling passageway serve to alter the air flow characteristics through the module and enhance the temperature reduction of the vapour as it passes through. These may also enhance collection of condensation droplets which may be later cleaned out of the vapour cooling passageway.

Figure 5A:
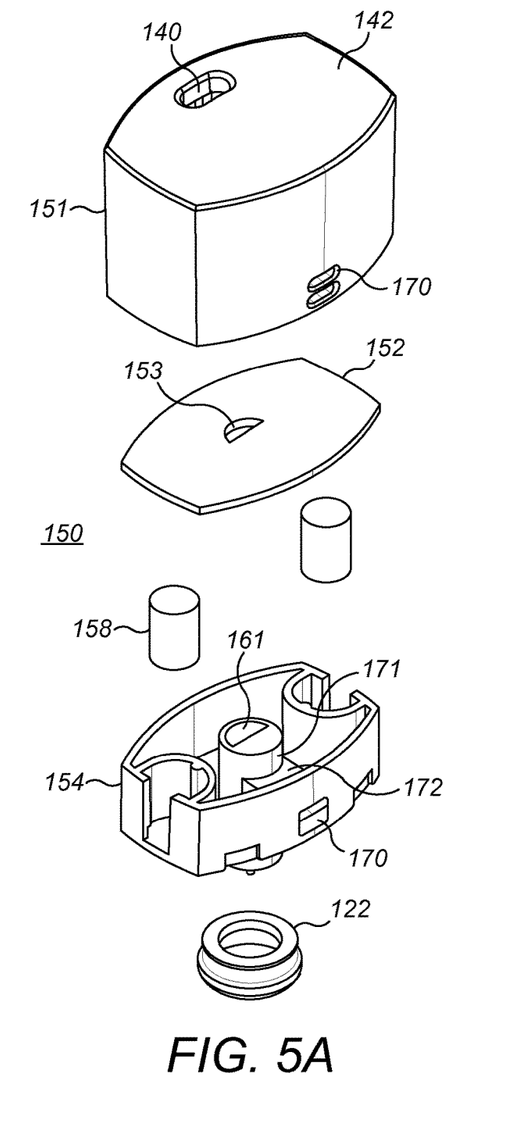
FIGS. 5A and 5B show an exploded view of a vapour cooling module according to the present invention.
Figure 5B:
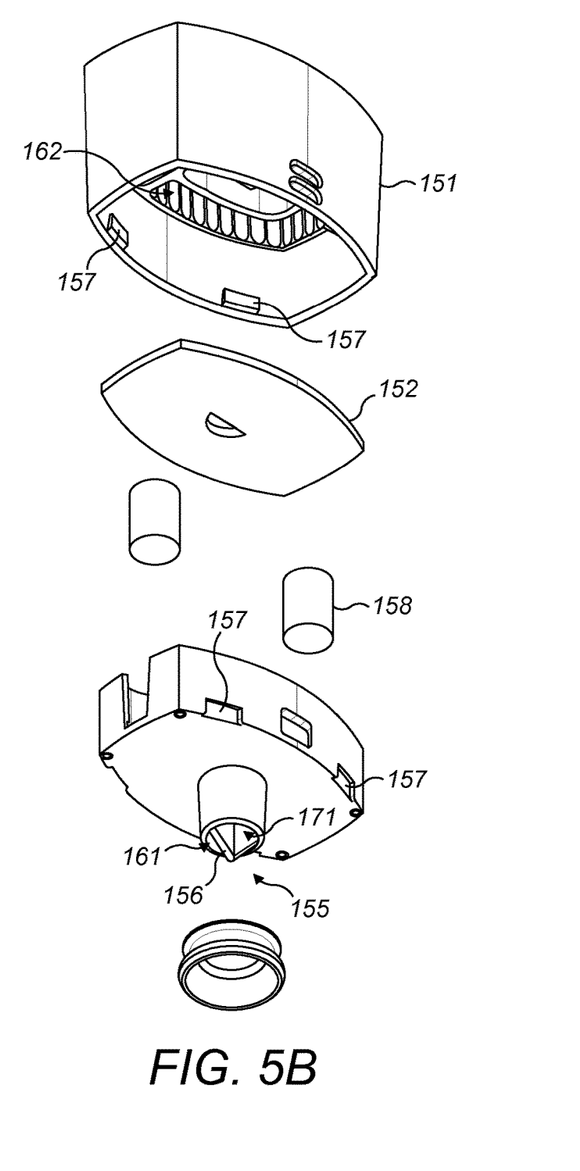

FIG. 5 shows an exploded view of an exemplary vapour cooling module 150 according to the present invention. A cap portion 151 provides the external shell of the module and retains the planar section 151 containing the second portion 162 of the vapour cooling passageway 160, as indicated in FIG. 5B. Openings in the cap portion 151 are positioned so as to correspond with the positions of the inhalation outlet 140 and the air inlet 170. In this example the cap portion 151 also serves as the mouthpiece and the upper surface 142 of the cap portion may outwards curve to a protruding lip around the inhalation outlet 140, as described above.

In this example, a connection portion 154 fits with the cap portion 152 to enclose the module on the chamber-interfacing side which, in use, connects with the remaining body of the device. It further provides the connection mechanism with the opening 121 in the body of the device and houses the first and second portions 171, 172 of the air inlet passageway and the first portion 161 of the vapour cooling passageway. The connection portion may be configured to closely fit within the cap portion 151 with cooperative fixation means 157 provided on the outer surface of the connection portion 154 and inner surface of the cap portion 151. The protrusion 155 extends from the bottom surface of the connection portion, as clearly illustrated in FIG. 5B, This Figure also shows the extended passageway divider 156, which separates the first portion 161 of the vapour-cooling passageway 160 and that of the aft inlet within the protrusion 155. The extended passageway divider 156 may extend into a point to enable it to pierce the wrapper of a cartridge within the chamber 120. As best seen in FIG. 5A, the first portion 161 of the vapour cooling passageway 160 extended from the opening in the protrusion upwards into the module 150. The aft inlet passage way follows a perpendicular path to the aft inlet 170 which corresponds with the opening in the cap portion 151 when assembled.

In this example an internal backing plate 152 acts as a gasket between the connection portion 154 and the second portion 162 of the vapour cooling passageway 160 within the cap portion 151. An opening 153 in the backing plate is positioned so as to correspond with the openings of the straight, first portion 161 and coiled, second portion 162 of the vapour cooling passageway 160, providing the essential fluidic connection.

The example of FIG. 5 illustrates an alternative connection mechanism to facilitate a removable attachment with the remaining portion of the body of the device. In this example, magnets 158 are retained with the vapour cooling module 150 which are positioned so as to align with corresponding magnetic material around the opening 121 to the chamber 120 in the remaining body portion of the device. These magnets 158 provide sufficient force to securely hold the vapour cooling module 150 in position but allow a user to apply a force to remove the module 150 when necessary.

In some examples of the device the top mouthpiece surface 142 of the vapour cooling module 150 may be removable to facilitate cleaning of the vapour cooling passageway.

The components of the device in contact with the vapour may be constructed from materials which readily accept heat from the vapour so as to accelerate the cooling process.

In addition to the above described examples of a coiled path and linearly extended path, many other modifications and variations of the vapour cooling module 150 and vapour cooling passageway 160 may be used to provide the primary technical effect of substantially cooling the vapour during transit between the chamber 120 and inhalation outlet 140.

In one such alternative configuration, the vapour cooling passageway 160 may have multiple curved portions or coiled portions within the second portion 162, for example each of the type shown in FIG. 4B. In such as arrangement the second portion 162 of the vapour cooling passageway is formed from multiple coiled portions, the coiled path of each being substantially confined to a neighbouring plane normal to the elongate axis and each in fluidic communication with adjacent coiled or curved portions. This arrangement would allow the length of the vapour cooling passageway to be significantly extended by adding a further coiled portion whilst only extending the length of the device by the thickness shown 151 in FIG. 4C.

Figure 6:
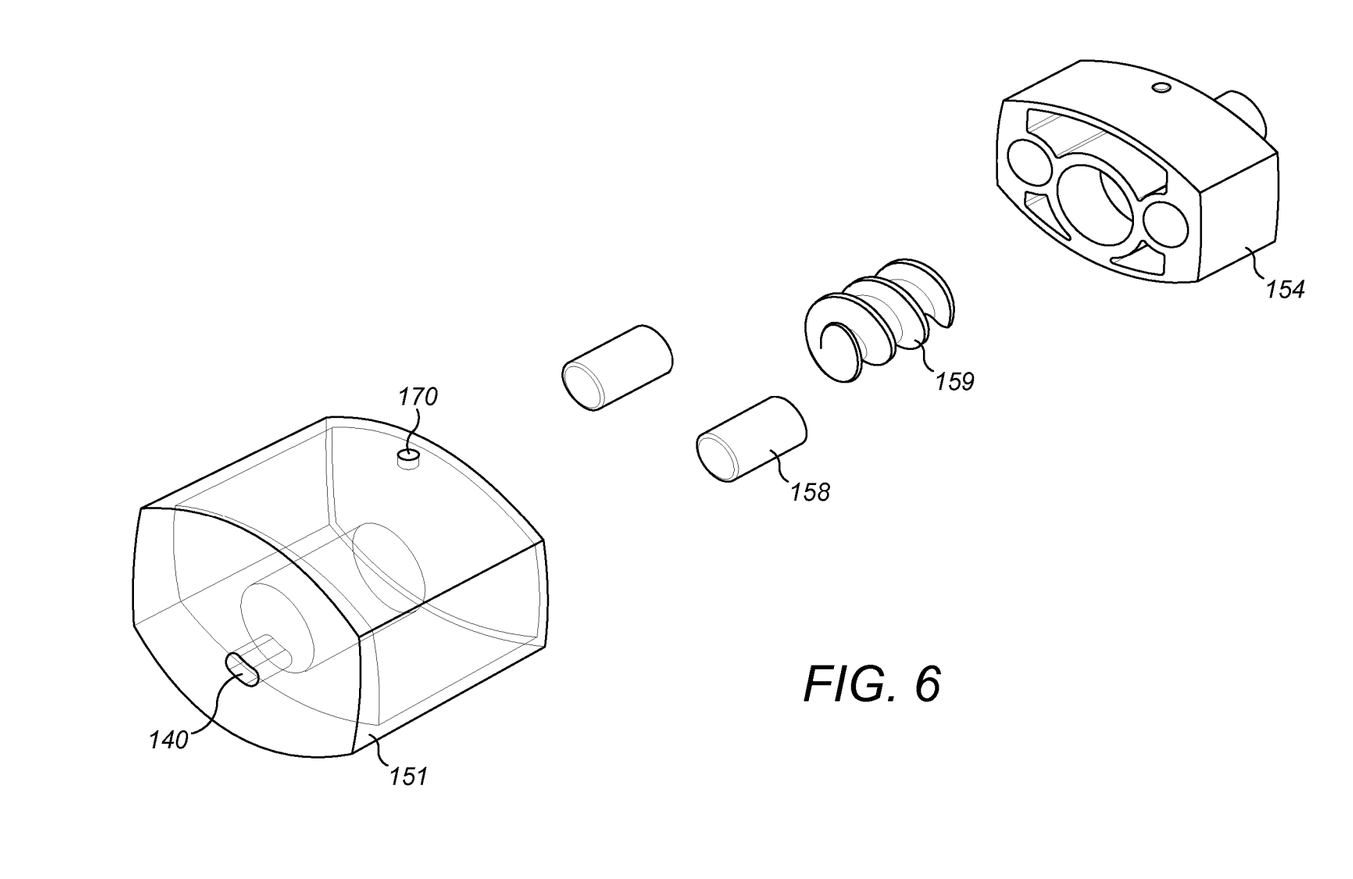
FIG. 6 shows an exploded view of a further vapour cooling module according to the present invention.

An alternative configuration of the vapour cooling module 150 is shown in FIG. 6. In this arrangement a helix component 159 is retained in an internal cavity of the vapour cooling module, the cavity defined by the cap portion 151 and connection portion 154 when connected together. The helix component 159 fits tightly, i.e. in an airtight manner within the cavity to provide the fluidic communication between the first portion 161 of the vapour cooling passageway and inhalation outlet 140. The helix component may be axially aligned with the longitudinal axis of the device thereby, in combination with the cavity, defining a helical path within the second portion 162 of the vapour cooling passageway 160. This arrangement therefore provides an alternative means to extend the vapour cooling passageway without substantially lengthening the module itself which is straightforward to manufacture and assemble. Furthermore the helix component 159 may be removed and cleaned to remove condensation, as is discussed further below.

In a further example, the characteristics of the generated vapour are improved further by careful configuration of the size of the air inlet 170 and inhalation outlet 140. A larger air inlet 170 may increase the flavour characteristics of the vapour by extracting an increased proportion of vapour from the chamber, whilst also providing a more optimal inhalation experience. Furthermore, improved cooling results may be produced if the diameter of the inhalation outlet is greater than the diameter of the air inlet. In other examples the size (or diameter) of the air inlet may be greater than that of the inhalation outlet. Furthermore, means for adjusting the diameter of the air inlet and inhalation outlet may be provided such that a user can select preferred vapour characteristics by adjusting the size of the inlet and outlet by appropriate control means. In further examples the diameter of the vapour cooling passageway is selected to improve optimum cooling effects. A passageway of substantially circular cross section and diameter of 4.5 mm (or an alternative shape with equivalent size to provide a similar cross-sectional area) was found to provide increased rate of cooling on a vapour passing through.

The total volume of the vapour cooling passageway may also be configured to optimise cooling. Examples of the present invention may provide substantial cooling if the total volume of the vapour cooling passageway is greater than 600 $mm^3$ or more preferably greater than 1000 $mm^3$ or more preferably still greater than 1800 $mm^3$. Since the vapour cooling module may be removable, alternative vapour cooling modules may be provided, each with differing dimensions of the vapour cooling passageway. This would allow a user to select a specific variation of vapour cooling module to suit his or her taste or that is appropriate for the particular material used.

An undesirable side-effect of the cooling of the vapour during transit between the chamber 120 and inhalation outlet 140 is the droplet condensation process that may occur within the vapour-cooling passageway 160. If this condensation is left within the device, after repeated use the internal components of the device may begin to degrade. Examples of the present invention may have additional features directed at solving or lessening the impact of condensation within the device. For example the top, mouthpiece surface 142 of the device may be removable to allow for removal of the vapour cooling passageway for cleaning. This may be achieved by providing a hinge on an edge of the end surface about which the top end surface may be rotatable to expose the internal components which may then be cleaned. Alternatively the second portion 162 of the vapour cooling passageway 160 and top surface 142 may form an integral component which may be released from the module 150, for example by a spring-biased push and release mechanism.

Considering the embodiments of FIGS. 4 and 5, for example, the planar section 151 containing the curved path of the second portion 162 may form a removable component to facilitate cleaning of the passageway. Alternatively the curved path of the second portion 162 of the vapour cooling passageway 160 may individually form a removable component. The periodic array of ridges 163 on the internal surfaces of the passageway may also enhance the collection of condensation droplets within the vapour-cooling passageway, which can then be cleared away by removing planar section 151 to facilitate cleaning of the internal passageway. This condensation collecting effect may be enhanced by coating the internal surfaces of the vapour cooling passageway of any device according to the present invention with a layer of material, such as a polymer material, which may increase absorption of the condensation.

In a further alternative directed at lessening the impact of condensation, the vapour cooling module or certain constituent parts thereof, such as the planar section 151 or the second portion 162 of the vapour cooling passageway, may be replaceable such that these parts may be disposed of and replaced if and when condensation or related degradation begins to have a detrimental effect on the operation of the device or the user's experience.

In a further example, the vapour-cooling passageway could comprise an additional disposable condensation-trapping part to substantially prevent condensation staying in contact with the functional internal components of the device. Such a part may take the form of a brush-like portion formed by an array of fibres or other alternative could be a polymer type product able to capture the condensation droplets which is positioned within the vapour cooling passageway to collect the condensation.

Another possibility utilises the possible additional feature of adjustable air inlet 170 and inhalation outlet 140 diameters. A user may adjust the air flow, for example by reducing the diameter of the air inlet 170 to increase the velocity of the air or vapour passing through the device. A high velocity air flow through the device may be used to expel any condensation within the device either through the inlet or outlet.

In another example of the aerosol generating device according to the present invention, the vapour-cooling passageway could include an additional flavour component to affect the flavour of the vapour generated within the chamber. This may be achieved by providing a flavour producing layer on the internal surface of parts of the passageway to impart additional flavour to the vapour coming into contact with the layer as it travels through the device. It may alternatively be provided by an additional filter component provided at the inhalation outlet or combined with the condensation trapping part described above. In examples of the present invention in which the portion of the vapour cooling module containing the vapour cooling passageway forms a removable component, this may allow a user to adjust the flavour by replacement of this component with alternatives containing differing flavour layers.

In some examples of the present invention the vapour-cooling passageway occupies at least 10% to 40% of the vapour-cooling module or mouthpiece of the device. The vapour-cooling passageway may preferably be located at the top part of the mouthpiece in connection with the air outlet and is preferably a non-uniform or closed structure such as a tube or serpentine structure. This allows the vapour generated to be in contact with the empty space of the internal volume of the mouthpiece as well as with the vapour-cooling passageway. Since the exterior surface of the tubular structure of the vapour-cooling structure may be exposed to the air within the internal volume of the mouthpiece, this may have an impact on the level of condensation observed in comparison with a vapour passing through a classical vapour cooling passageway known in the prior art, which may be embedded or enclosed within the body of the device.

The examples of the present invention described above provide an aerosol generating device which overcomes several of the problems of prior art devices. In particular, by providing a vapour-cooling module between the heated chamber and the inhalation outlet, the generated vapour may be substantially cooled to a level acceptable for pleasurable inhalation and any harsh effects are mitigated. This allows for the vapour to be cooled independently of the dilution of the vapour, unlike devices which use the addition of ambient air to cool the vapour. Examples of the invention cool the vapour by using an extended vapour cooling passageway which provides a low cost, easy to manufacture means to cool a vapour in comparison to solutions using active cooling components. Further examples use curved configurations of the vapour cooling passageway so as to maximise the cross sectional area of the device utilised such that the length of the vapour cooling passageway may be extended without extending the overall length of the device.

The invention claimed is:

1. An aerosol generating device having a longitudinal axis, comprising:
    an inhalation outlet;
    a chamber for holding a material, the material capable of generating a vapour when heated;
    a heater for heating the material held in the chamber; and
    a vapour-cooling module having a vapour-cooling passageway providing a fluidic connection between the chamber and the inhalation outlet,
    wherein, in use, suction at the inhalation outlet whilst heating the material in the chamber, causes vapour generated in the chamber to pass through the vapour-cooling passageway to the inhalation outlet, the vapour-cooling passageway defining a length that reduces a temperature of the vapour as the vapour is transported through the vapour-cooling passageway, and
    wherein a portion of the vapour-cooling passageway follows a coiled path confined to a plane extending substantially orthogonal to the longitudinal axis.

2. The device of claim 1 wherein a volume of the vapour-cooling passageway is 600 mm$^3$ or greater.

3. The device of claim 1 further comprising:
    an air inlet fluidly connected by an air inlet passage to the chamber.

4. The device of claim 3 wherein the vapour-cooling passageway is substantially longer than the air inlet passage.

5. The device of claim 1 wherein a portion of the vapour-cooling passageway is substantially linear.

6. The device of claim 1 wherein a portion of the vapour-cooling passageway is substantially helical.

7. The device of claim 1 wherein the vapour-cooling passageway has multiple curved portions each substantially confined to a neighbouring parallel plane.

8. The device of claim 1 wherein the coiled path substantially fills a cross sectional area of the device.

9. The device of claim 1, wherein the coiled path is formed in a removable component of the vapour-cooling module.

10. The device of claim 1 wherein a cross-sectional area of the vapour-cooling passageway varies along its length.

11. The device of claim 3 wherein one or both of the air inlet and the inhalation outlet is adjustable in size.

12. The device of claim 3 wherein the size of the inhalation outlet is always greater than the size of the air inlet or vice versa.

13. The device of claim 1 wherein the heater is configured to heat but not burn the material held in the chamber.

14. The device of claim 1 wherein the chamber is configured to receive a cartridge containing the material and the heater is configured to heat the material within the cartridge.

15. The device of claim 1 wherein the vapour-cooling module is positioned at one end of the device and the inhalation outlet is positioned on the vapour cooling module such that the vapour-cooling module acts as a mouthpiece.

16. The device of claim 1 wherein the vapour cooling module forms a detachable component such that the vapour-cooling module is removable to expose the chamber.

17. The device of claim 16 wherein a chamber-interfacing end of the detachable vapour cooling module comprises a protrusion that provides a fluidic connection with the chamber.

18. The device of claim 17 further comprising an air inlet connected by an air inlet passage to the chamber, wherein the air inlet is provided in the vapour cooling module and the air inlet passage also runs through the protrusion, alongside but separated from the vapour-cooling passageway.

19. The device of claim 17 wherein the chamber interfacing end of the protrusion is pointed such that it may pierce a cartridge held in the chamber upon connection of the vapour-cooling module to the device.

20. An aerosol generating device having a longitudinal axis, comprising:
an inhalation outlet;
a chamber for holding a material, the material capable of generating a vapour when heated;
a heater for heating the material held in the chamber; and
an extended vapour-cooling passageway providing a fluidic connection between the chamber and the inhalation outlet, a portion of the vapour-cooling passageway defining a coiled path confined to a plane extending substantially orthogonal to the longitudinal axis, wherein at least a portion of the vapour-cooling passageway forms a removable component of the device.

21. The device of claim 20 wherein the vapour-cooling passageway defines a curved path portion, the curved path portion of the vapour-cooling passageway formed in the removable component of the device.

22. The device of claim 21 wherein the curved path portion of the vapour-cooling passageway follows a substantially helical path.

23. The device of claim 20 wherein the coiled path substantially fills a cross sectional area of the device.

24. The device of claim 21 wherein the curved path portion of the vapour-cooling passageway is formed of multiple consecutive coiled sections each substantially confined to a neighbouring parallel plane.

25. A kit comprising:
the device of claim 1 and a cartridge containing a material capable of generating a vapour when heated.

* * * * *